Figure 1:
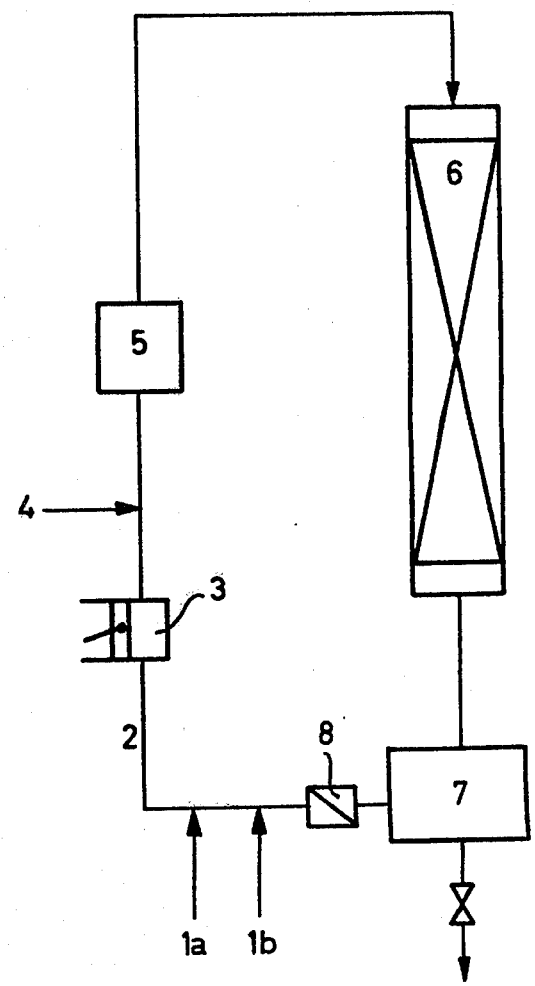

United States Patent [19]

Weitz et al.

[11] 4,189,600
[45] Feb. 19, 1980

[54] MANUFACTURE OF GLYCOL ACETATE

[75] Inventors: Hans-Martin Weitz, Bad Durkheim; Juergen Hartig, Ludwigshafen; Ludwig Vogel, Frankenthal;; Helmuth Grube, Bad Durkheim, all of, Fed. Rep. of Germany

[73] Assignee: BASF Aktiengesellschaft, Fed. Rep. of Germany

[21] Appl. No.: 816,737

[22] Filed: Jul. 18, 1977

[30] Foreign Application Priority Data

Aug. 14, 1976 [DE] Fed. Rep. of Germany ....... 2636669

[51] Int. Cl.$^2$ .............................................. C07C 67/05
[52] U.S. Cl. ..................................... 560/246; 560/241
[58] Field of Search ....................... 560/241, 247, 246

[56] References Cited

U.S. PATENT DOCUMENTS

| 2,519,754 | 8/1950 | Gresham et al. | 560/246 |
| 3,479,395 | 11/1969 | Huguet | 560/246 |
| 3,668,239 | 6/1972 | Kollar | 560/246 |
| 3,715,389 | 2/1973 | Hoch et al. | 560/106 |
| 3,770,813 | 11/1973 | Kollar | 560/246 |

FOREIGN PATENT DOCUMENTS 1931563 7/1970 Fed. Rep. of Germany .
2410570 9/1975 Fed. Rep. of Germany .

Primary Examiner—Bernard Helfin
Assistant Examiner—L. Hendriksen
Attorney, Agent, or Firm—Keil & Witherspoon

[57] ABSTRACT

Diacetates of 1,2-glycols are manufactured by reacting acetic acid with an olefin and oxygen, using oxygen dissolved in the liquid phase of the reaction mixture and avoiding the presence of gaseous oxygen in the reaction space.

4 Claims, 2 Drawing Figures

MANUFACTURE OF GLYCOL ACETATE

The present invention relates to a process for the manufacture of acetic acid esters of 1,2-diols (glycols) by reacting an olefin with acetic acid and molecular oxygen in the presence of a catalyst.

This reaction used for the manufacture of the glycol acetates, especially the acetates of ethylene glycol and of 1,2-propylene glycol, is also referred to as oxidative acylation of olefins. It can also be carried out with carboxylic acids other than acetic acid, but for economic reasons only acetic acid is used as the carboxylic acid. Various processes for carrying out the reaction have been proposed, essentially differing from one another in respect of the choice of particular catalysts.

According to French Pat. No. 1,421,288, a bromide, with or without a metal salt, may be used; the solvent used is a mixture of the carboxylic acid with an aromatic hydrocarbon.

According to French Pat. No. 1,419,966, noble metals of group VIII of the periodic table of the elements are used, with nitric acid or nitrates serving as oxygen donors or oxidizing agents.

U.S. Pat. No. 3,542,857 discloses the use of cerium salts, soluble in carboxylic acids, as catalysts.

U.S. Pat. No. 3,262,969 discloses the catalytic action of redox systems containing alkali metal halides and palladium salts.

According to German Laid-Open Application DOS No. 1,931,563, iodine, and iodine compounds with cations of heavy metals or alkali metals are suitable catalysts for the process in question. The suitability of bromine or chlorine for use in a similar system which additionally contains metal cations which can exhibit more than one valency (for example tellurium, cerium, arsenic, antimony, manganese and cobalt) has also been disclosed.

Further comparable systems are disclosed in German Laid-Open Application DOS No. 2,226,505 and British Pat. No. 1,058,995.

Different catalyst systems are disclosed in German Laid-Open Applications Dos No. 2,260,822, 2,356,389 and 2,256,847. These systems comprise certain complex compounds of certain transition metals from amongst zirconium, hafnium, niobium, tantalum, molybdenum, tungsten and rhenium with, for example, alkali metals, titanium, vanadium, chromium, manganese, iron, cobalt, nickel, copper, zinc, aluminum or silver.

According to a proposal in co-pending patent application Ser. No. 792,697 now U.S. Pat. No. 4,122,286 (the disclosure of which is hereby incorporated by reference) 1,2-glycol esters may be obtained by reacting an olefin with molecular oxygen and a carboxylic acid in the presence of a catalyst based on a compound of orthotitanic acid with a low molecular weight alcohol and/or with a low molecular weight carboxylic acid.

In all the improvements hitherto disclosed for this process, the olefin and acetic acid are reacted with gaseous oxygen in the presence of homogeneous or heterogeneous catalysts; it is true that the reaction evidently occurs in solution, but the oxygen consumed is always replaced from the gas phase.

Of course, it is a disadvantage of the conventional embodiments of the process that explosive gas mixtures may be formed; this is particularly true in the event of a breakdown, ie. if the oxygen conversion drops for any reason.

To avoid the formation of ignitable mixtures, it has been proposed to lower the oxygen concentration by adding chemically inert gases, eg. nitrogen, argon or carbon dioxide. However, the consequence of this is that the rate of reaction, ie. the conversion per unit time, decreases; furthermore, the expenditure on control and other equipment is increased.

It is an object of the present invention to avoid the above disadvantages.

We have found that this object is achieved and that the process for the manufacture of acetic acid esters of 1,2-diols (glycols) by reacting an olefin with acetic acid and molecular oxygen in the presence of a catalyst can be carried out with high selectivity and high space-time yield, without hazard and without the formation of undesirable by-products, if the oxygen is dissolved in at least one liquid reactant, or in the recycled reaction mixture, outside and immediate reaction space and the reaction is carried out with dissolved oxygen.

Accordingly, the improvement of the process described at the outset, and hence the invention, further comprises charging the reaction space with an amount of liquid which is more or less saturated in oxygen, and/or using an amount of liquid which suffices at all times to dissolve completely the amount of gas introduced. In this way, safe operating conditions are achieved. In the present context, the term "saturated" need not always mean that the limit of solubility of oxygen is reached; the conditions should merely tend toward this objective.

Advantageously, the formation of a gas phase in the reaction space is entirely prevented by working under pressure and using a reaction space which automatically discharges any coherent amounts of gas which may be formed, provided these amounts are more than just individual discrete bubbles.

The admixture of the gases—oxygen, with or without olefin— to the reaction mixture or to a liquid reactant may be effected by means of conventional equipment; for example an ejector, or a flow tube packed with a material having a large surface area, or with suitable packings, may be employed.

The amount of gas which is soluble in the reaction mixture under the operating conditions is indicated by the solubility coefficient or can easily be determined in every case by a preliminary experiment. In order to give a picture of the practical effect of the invention, the solubility of oxygen at various temperatures in acetic acid, and the critical curve of mixtures of propene and acetic acid or propionic acid are given below. Of course, all the other constituents of the reaction mixture also influence the solubility, so that general data applicable to all conceivable cases cannot be given. Of course, the reaction does not depent on the amount of oxygen corresponding to the solubility being actually dissolved in the mixture. Rather, amounts of oxygen below the solubility limit may, in given circumstances, suffice to achieve a sufficient reaction rate.

TABLE 1

Solubility of oxygen in acetic acid; solubility coefficient $\alpha$ defined as $\alpha$ = ml (S.T.P.) of oxygen/g of solvent.bar

| Temperature (°C.) | $\alpha$ (Acetic acid) |
|---|---|
| 25 | 0.190 |
| 100 | 0.186 |
| 180 | 0.154 |

TABLE 2

| Critical curve of the binary systems propylene/acetic acid | | |
|---|---|---|
| °C. | bar | mole % of $C_3H_6$ |
| 91.4 | 46.0 | 100[a] |
| 120 | 62.9 | 90.1 |
| 149 | 83.6 | 70.4 |
| 200 | 99.1 | 53.1 |
| 236 | 89.1 | 38.2 |
| 321.6 | 58.0 | 0[a] |

[a]Critical point of $C_3H_6$ and $CH_3COOH$ respectively.

The conversions and space-time yields which are achievable by means of the invention, on the basis of the above quantitative data, may be seen from the Examples which follow later. FIG. 1 of the accompanying drawings shows a suitable reaction arrangement.

The reactor (6) consists of a 4 m long jacketed steel tube of internal diameter 20 mm. The reaction temperature is regulated by means of a variable flow of steam through the jacket.

The starting materials may be introduced at the top or at the bottom. The schematic drawing relates to the former embodiment.

Acetic acid and liquid olefin are fed from separate vessels through product lines (1a, b), by means of pumps into the reaction system. To prevent the raw materials from flowing directly into the separator (7), a non-return valve (8) is provided between (1) and (7). The liquid reaction mixture is fed to the intake side of the pump (3) through the product line (2). On the output side of the pump (3), the gaseous oxygen (4) is fed in. The mixing device (5) which ensures that the oxygen introduced dissolves completely in the liquid mixture consists of a long tube filled with packings, or of an ejector. In order to check whether the oxygen has dissolved completely, a sight glass and control devices are provided behind the mixing unit and permit the elimination of gaseous materials by the conventional method.

The product mixture issuing from the reactor passes into the buffer vessel (separator, 7); the amount discharged is controlled by a pressure regulating system (8,9). If required, a part of the mixture can be recycled into the installation.

Of course, a horizontal reactor can be used instead of the vertical reactor. A vertical reactor is particularly advantageously operated in the ascending direction, because any residual gases can in this way easily be separated off. The catalyst packing may have to be secured by mechanical means to prevent it floating, if the catalyst is very fine. If homogeneous catalysts are used, the reaction space, which in other cases is empty, is advantageously charged with some type of packing which ensures uniform flow.

Obviously the shape of the reactor is not restricted to a more or less squat tower; instead, the reactor may also be, for example, a tubular loop or coil. Though continuous operation offers advantages, the process can also be carried out batchwise in the conventional equipment.

Figure 2:
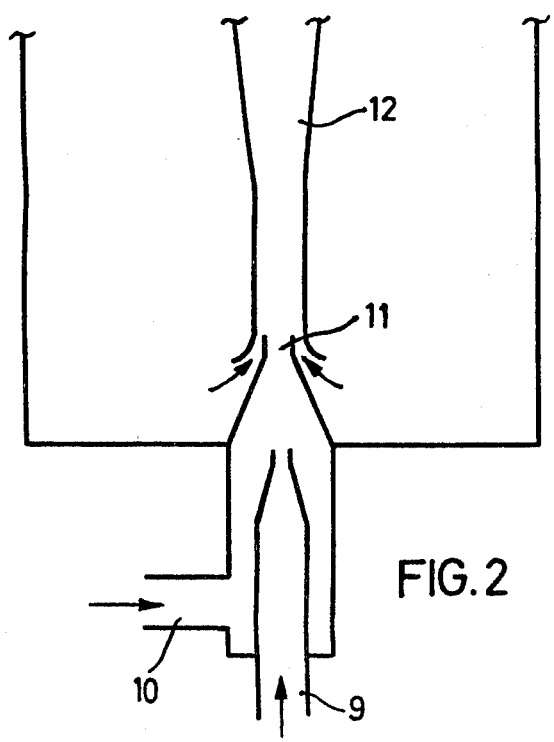

If an ejector is used as the mixing device, it may be constructed, for example, in the manner shown in FIG. 2 of the accompnaying drawings. The liquid is fed in at (9) under the appropriate input pressure and entrains gas, fed in at (10), in the conventional manner; an after-mixing zone (11) may be provided. If the pressure in the space (12) filled with liquid is higher than the pressure of the gas fed in, the effectiveness of the device decreases with increasing saturation of the liquid with the gas. This fact may be used in the conventional manner to regulate the gas feed. Suitable mixing devices of the stated type are disclosed, for example, in German Laid-Open Application DOS No. 2,410,570.

The reaction temperature is in general from 60° to 210° C., preferably from 120° to 170° C. Whilst temperatures below 60° C. are possible in principle, the space-time yield drops rapidly. Temperatures above 210° C. are also possible, but the formation of by-products is increased.

The reaction pressure is in general from atmospheric pressure to about 300 bars, depending on the procedure. Pressures of from 20 to 100 bars are preferred.

Amongst the olefins which may be used to carry out the process of the invention, ethylene and propylene are preferred in view of the commercial importance of the end products obtained; in principle it is, however, also possible to convert higher olefins to the corresponding glycol esters by a corresponding reaction.

It is true that in general acetic acid itself serves as the solvent for carrying out the reaction; in special cases, however, the use of an oxidation-resistant auxiliary solvent, eg. an aromatic hydrocarbon, is readily possible. The end products formed can in principle also be used as solvents.

The reaction mixture may additionally contain by-products which are formed in the reaction, separated off in the course of the subsequent working-up, and recycled. Examples are allyl acetate and isopropyl acetate, which are formed during the oxidative acetylation of propylene and may serve as constituents of a solvent.

Suitable catalysts for the process of the invention are in the main those mentioned at the outset.

Catalyst systems to be singled out are those mentioned in French Pat. No. 1,421,288, U.S. Pat. No. 3,262,969, German Laid-Open Applications DOS No. 1,931,563 and 2,226,505 and British Pat. No. 1,058,995, as well as those disclosed in German Laid-Open Applications DOS Nos. 2,260,822, 2,356,389 and 2,256,847.

In the process of the invention, it is particularly advantageous to use a catalyst based on a compound of orthotitanic acid with a (low molecular weight) alcohol and/or a (low molecular weight) carboxylic acid. This catalyst may be used in solution (ie. in a homogeneous form) or as a precipitate on a suitable carrier, for example active charcoal.

All the catalysts are used in the conventional catalytic amounts, or as suitably arranged solids; the latter may be fixed, or suspended in the reaction mixture.

The glycol esters which may be manufactured in accordance with the invention are used extensively as intermediates, solvents and plasticizers.

Since the hydrolysis of the esters in general proceeds smoothly and simply, the glycols on which the esters are based also become accessible by the invention. When the glycols are produced, the acid liberated by hydrolysis may be recycled to the process. The acetic acid to be used in the reaction may, in this case, be recycled as such or in the form of an ester, in which latter case it is necessary to ensure that the reaction mixture possesses hydrolytic properties and is thus able to provide free acetic acid for carrying out the reaction.

In the Examples which follow, amounts are by weight.

EXAMPLE 1

53.3 g of palladium chloride and 12.0 g of tellurium dioxide are dissolved in 4,000 ml of 6 N hydrochloric acid; 500 g of active charcoal (from 0.2 to 0.4 mm $\phi$), which has beforehand been boiled with 15 percent strength nitric acid, are added and the mixture is slowly evaporated to dryness on a waterbath. After further drying by passing a stream of nitrogen gas at 150° C. through the catalyst in a tube for 20 hours, the material is reduced by passing a stream of nitrogen gas, which has been saturated with methanol at room temperature, into the tube at a rate of 50 l/minute for 10 hours at 200° C. and 10 hours at 400° C.

0.5 l of the catalyst thus produced is filled into a pressure-resistant reaction tube (length 4,000 mm, diameter 20 mm). Glass rings are introduced into the tube above and below the catalyst. 0.5 l of liquid propene, 3 l of acetic acid and as much oxygen as has dissolved in the ejector are then passed per hour through the reactor at 38 bars and 170° C. A sight glass is provided upstream from the reactor, in order to check whether the oxygen has dissolved completely.

The solution thus obtained is fed into the bottom of the reactor. The reaction product which issues is fed into a separator from where it is continuously withdrawn from the installation.

Over a period of 50 hours, the space-time yield (g of propanediol monoacetate and diacetate/l of reaction space. h) averages 120.

In addition to 1,2-propanediol diacetate (and small amounts of the monoacetates), allyl acetate is obtained, in a space-time yield of 70 g/l.h.

EXAMPLE 2

The reactor is a glass-lined pressure-resistant steel tube which has an internal diameter of 25 mm and a length of 2 m. It is filled with packings (hollow spheres of stainless steel through which the reaction mixture can flow) and is charged, under a pressure of 35 bars and at an operating temperature of 170° C., with a mixture of acetic acid, propylene and dissolved oxygen, together with the catalyst dissolved in methanol or acetic acid.

Per hour, 6 l of acetic acid, from 200 to 800 ml of liquid propylene and varying amounts of catalyst solution are combined in a continuous mixing device, the acetic acid first having been saturated with oxygen in an adjustable ejector. The mode of action of the latter is illustrated in FIG. 2. A liquid level regulator ensures that no gaseous oxygen can leave the mixing device. The remaining constituents are added by means of metering pumps to the homogeneous oxygen-containing solution obtained above and the solution is then introduced into the reaction space as described. At a solution temperature of 40° C., 0.15 ml (S.T.P.) of oxygen are dissolved per gram of acetic acid and per bar; this corresponds to the experimentally determined solubility product.

At the stated operating temperature, propylene glycol acetate is obtained in varying amounts, depending on the residence time and the composition of the mixture (compare the Table). As a rule, the conversion of oxygen is complete.

TABLE

| Catalyst system | Amount (g/l of acetic acid) | Space-time yield (g/l of reaction mixture) |
|---|---|---|
| $Ti_2O(OAc)_6$ | 3.5 | 52 |
| $TeI_4$ | 9.3 | 84 |
| $TeO_2 + I_2$ | 6.3 + 47.8 | 182 |
| $[Ti(acetyl\ acetonate)_3]_2[TiCl_6]$ | 2.4 | 93 |
| $TeO_2 + HBr$ | 23.3 + 43.3 | 140 |
| $Co(OAc)_2 + CoBr_2$ | 4.2 + 3.7 | 74 |

We claim:

1. An improved process for the manufacture of an acetic acid ester of 1,2-diol by reacting an olefin with acetic acid and molecular oxygen in the presence of a catalyst in a reactor, wherein the improvement comprises:
   dissolving the oxygen in at least one liquid reactant or in the recycled liquid reaction mixture outside the reactor,
   charging the reactor with said liquid reactant or liquid reaction mixture containing dissolved oxygen, and
   carrying out the reaction of the olefin and acetic acid with oxygen while simultaneously removing any gas formed in the reactor, whereby the formation of a gas phase in the reactor is prevented 2. A process as claimed in claim 1, wherein the acetic acid, which is liquid, is saturated with oxygen at from atmospheric pressure to about 100 bars.

3. A process as claimed in claim 2, wherein the saturation with oxygen is carried out in an ejector equipped with means of regulating the oxygen feed.

4. A process as claimed in claim 1, carried out at 120 to 170° C. and 20 to 100 bars.

* * * * *